United States Patent
Magdolen et al.

(12) United States Patent (10) Patent No.: US 7,208,521 B2
(45) Date of Patent: Apr. 24, 2007

(54) SELECTIVE INHIBITORS OF THE UROKINASE PLASMINOGEN ACTIVATOR

(75) Inventors: Viktor Magdolen, Kirchheim (DE); Luis Moroder, Martinsried (DE); Stefan Sperl, Pullach (DE); Jörg Stürzebecher, Erfurt-Rhoda (DE); Olaf Wilhelm, München (DE)

(73) Assignee: Wilex AG, Munich (DE)

( * ) Notice: Subject to any disclaimer, the term of this patent is extended or adjusted under 35 U.S.C. 154(b) by 114 days.

(21) Appl. No.: 11/058,699

(22) Filed: Feb. 16, 2005

(65) Prior Publication Data

US 2005/0215642 A1    Sep. 29, 2005

Related U.S. Application Data

(62) Division of application No. 10/049,634, filed as application No. PCT/EP00/08234 on Aug. 23, 2000, now Pat. No. 7,049,460.

(30) Foreign Application Priority Data

Aug. 25, 1999  (DE)  ................. 199 40 389

(51) Int. Cl.
  *A61K 31/24*  (2006.01)
  *B65D 69/00*  (2006.01)
(52) U.S. Cl. ............. 514/540; 514/595; 514/634; 206/569; 206/568
(58) Field of Classification Search ........ 514/540, 514/595, 634; 206/568, 569
See application file for complete search history.

(56) References Cited

U.S. PATENT DOCUMENTS

| 3,257,411 A | 6/1966 | Patchett et al. |
| 5,914,319 A | 6/1999 | Schacht et al. |

FOREIGN PATENT DOCUMENTS

| CH | 441366 A | 1/1968 |
| DE | 947552 C | 9/1956 |
| WO | WO 9920608 A | 4/1999 |

OTHER PUBLICATIONS

Carter et al., Chemotherapy of Cancer, second edition, John Wiley & Sons, N.Y., N.Y., 1981, pp. 362-365.*
Y. Heechung et al., "Selective Inhibition of Urokinase by Substituted Phenylguanidines: Quantitative Structure-Activity Relationship Analyses," Journal of Medicinal Chemistry, American Chemical Society, vol. 33, No. 11, 1990, p. 2956-2961.
R. Rai et al., "Guanidinophenyl-substituted enol lactones as selective, mechanism-based inhibitors of trypsin-like serine proteases," Journal of Medicinal Chemistry, vol. 35, No. 22, 1992, p. 4150-9.
W. Bollag et al. "Substituted Benzylhydrazines", Chemical Abstracts, vol. 69, No. 9, Aug. 26, 1968, abstract No. 35691c, p. 3321.

* cited by examiner

*Primary Examiner*—Shailendra Kumar
(74) *Attorney, Agent, or Firm*—Rothwell, Figg, Ernst & Manbeck (57) ABSTRACT

The present invention relates to novel selective inhibitors of the urokinase plasminogene activator (uPA, EC3,4.21.31) of the aryl guanidine type.

38 Claims, 2 Drawing Sheets

SELECTIVE INHIBITORS OF THE UROKINASE PLASMINOGEN ACTIVATOR

CROSS-REFERENCE TO RELATED APPLICATION

This application is a divisional of application Ser. No. 10/049,634 filed Feb. 25, 2002, now U.S. Pat. No. 7,049,460, which is a national stage entry of International Application No. PCT/EP00/08234, filed Aug. 23, 2000, which International Application claims priority from German Application DE 19940389.9, filed Aug. 25, 1999.

The present invention relates to novel selective inhibitors of the urokinase plasminogen activator (uPA, EC 3.4.21.31) of the arylguanidine type.

The urokinase-type plasminogen activator (uPA) plays a key part in tumor invasion and formation of metastases (Schmitt et al., J. Obst. Gyn. 21 (1995), 151–165). uPA is overexpressed in various types of tumor cells (Kwaan, Cancer Metastasis Rev. 11 (1992), 291–311) and binds to the tumor-associated uPA receptor (uPA-R) in which activation of plasminogen to plasmin takes place. Plasmin is capable of degrading various components of the extracellular matrix (ECM) such as fibronectin, laminin and collagen type IV. It also activates some other ECM-degrading enzymes, in particular matrix metalloproteinases. High amounts of tumor-associated uPA correlate with a higher risk of metastasizing in cancer patients (Stephens et al., Breast Cancer Res. & Treat. 52 (1998), 99–111). Therefore, inhibition of the proteolytic activity of uPA is a good starting point for an anti-metastatic therapy.

A common feature of many known synthetic uPA inhibitors is a basic residue containing amidino or guanidino groups, which can bind to $Asp^{189}$ in the uPA S1 specificity pocket and which acts as an arginine mimetic there (Spraggon et al., Structure 3 (1995), 681–691). However, most of the known inhibitors are not selective for uPA but also inhibit other serine proteases such as trypsin, thrombin, plasmin or tissue plasminogen activator (tPA).

p-Aminobenzamidine is a moderately selective uPA inhibitor having an inhibition constant of 82 μM. Billstroem et al. (Int. J. Cancer 61 (1995), 542–547) could show a distinct decrease in the growth rate of DU145 tumors (a prostate adenocarcinoma cell line) in SCID mice when administering orally a daily dose of 125 to 250 mg of p-aminobenzamidine/kg/day. The side effects were negligible.

Some monosubstituted phenylguanidines have proved effective and selective uPA inhibitors in vitro. These small molecules show inhibition constants in the micromolar range but they bind only in the S1 pocket of uPA (Yang et al., J. Med. Chem. 33 (1990), 2956–2961). Biological studies using these compounds were not carried out.

The diuretic amiloride is a selective uPA inhibitor (Ki, uPA=7 μM) which prevents the formation of lung metastases after i.v. inoculation of rat breast adenocarcinoma cells (Kellen et al., Anticancer Res. 8 (1988), 1373–1376). Some 3-amidinophenylalanine derivatives have likewise proved effective inhibitors of serine proteases but these compounds generally have only low selectivity for uPA (Stürzebecher et al., J. Med. Chem. 40 (1997), 3091–3099; Stürzebecher et al., J. Enzyme Inhib. 9 (1995), 87–99).

Currently the most effective and most selective uPA inhibitors are benzo[b]thiophene-2-carboxamidine derivatives (B428 and B623: $K_{i, uPA}$=0.32 and 0.07 μM, respectively; U.S. Pat. No. 5,340,833). Rabbani et al. (Int. J. Cancer 63 (1995), 840–845) and also Xing et al. (Cancer Res. 57 (1997), 3585–3593) could show, after administration of 4-iodobenzo[b]thiophene-2-carboxamidine (B428), a decrease of tumor growth and metastases formation in a syngeneic model of rat prostate cancer and mouse breast cancer, respectively. The latter studies showed a further decrease in primary tumor growth when B428 was administered together with the antiestrogen tamoxifen.

It was the object of the present invention to provide novel selective uPA inhibitors. This object is achieved by novel arylguanidine and in particular phenylguanidine derivatives. These compounds contain a further substituent on the aromatic ring system, preferably in para position to the guanidine group, which substituent contains an unsubstituted or substituted methylene group followed by hydrogen donor/acceptor functionalities. Owing to this substitution pattern, the compounds are particularly effective and selective for uPA. This efficacy could be attributed possibly to the fact that they (1) interact as arginine mimetics with the $Asp^{189}$ amino acid residue in the S1 pocket of uPA and
(2) can interact with the S2 and/or S3 pockets of uPA.

N-Substituted p-aminophenylguanidines (without methylene spacer) and also p-guanidinophenylalanine derivatives (2 methylene groups as spacer) were ineffective uPA inhibitors. The compounds of the invention preferably contain urethane or urea groups for interaction with S2 and/or large hydrophobic radicals such as aryl groups or cycloalkyl groups (e.g. adamantane) for interaction with S3.

The present invention thus relates to the use of compounds of the formula I in which Ar is an aromatic or heteroaromatic ring system, $X^1$ is $NR^3R^4$, $OR^3$, $SR^3$, $COOR^3$, $CONR^3R^4$ or $COR^5$, $R^1$ is H, an unsubstituted or substituted alkyl, alkenyl, alkynyl, aryl or/and heteroaryl radical, or $COOR^3$, $CONR^3R^4$ or $COR^5$, $R^2$ is halogen, $C(R^6)_3$, $C_2(R^6)_5$, $CO(R^6)_3$ or $OC_2(R^6)_5$, $R^3$ is H or any organic radical, $R^4$ is H or an unsubstituted or substituted alkyl, alkenyl or alkynyl radical, $R^5$ is H, an alkyl, alkenyl, alkynyl, carboxyalkyl, carboxyalkenyl, carboxyalkynyl, carboxyaryl or carboxyheteroaryl radical, where the alkyl, alkenyl, alkynyl, aryl and heteroaryl radicals may be unsubstituted or substituted, $R^6$ is in each case independently H or halogen, in particular F, and m is an integer from 0 to 4, or salts of said compounds for preparing an agent for inhibition of the urokinase plasminogen activator.

The compounds may be present as salts, preferably as physiologically tolerated acid salts, for example as salts of mineral acids, particularly preferably as hydrochlorides or as salts of suitable organic acids. The guanidinium group may carry, where appropriate, protective functions which are removable by cleavage, preferably under physiological conditions. The compounds may be present as optically pure compounds or as mixtures of enantiomers or/and diastereoisomers.

In the compounds of the general formula (I), Ar is preferably an aromatic or heteroaromatic ring system having a single ring, in particular a benzene ring. In this ring system the substituents $CHX^1R^1$ and $NHC(NH)NH_2$ are preferably arranged in meta or para position and particularly preferably in para position. In addition, Ar may further contain other, non-hydrogen substituents $R^2$. The number of substituents $R^2$ is preferably 0, 1, 2 or 3, particularly preferably 0 or 1 and most preferably 0. Preferred examples of $R^2$ are halogen atoms (F, Cl, Br or I), $CH_3$, $CF_3$, OH, $OCH_3$ or $OCF_3$.

The substituent $—CHX^1R^1$ is critical for inhibitor activity. $R^1$ may be H or an unsubstituted or substituted alkyl, alkenyl, alkynyl, aryl or/and heteroaryl radical. The alkyl radical may be a straight-chain or branched $C_1$–$C_{10}$-alkyl group, in particular a $C_1$–$C_4$-alkyl group or a $C_3$–$C_8$-cycloalkyl group which may be substituted with, for example, $C_1$–$C_3$-alkoxy, hydroxyl, carboxyl, amino, sulfonyl, nitro, cyano, oxo or/and halogen or else with aryl or heteroaryl radicals. Alkenyl and alkynyl radicals are preferably $C_2$–$C_{10}$ groups, in particular $C_2$–$C_4$ groups which may be unsubstituted or substituted as described above. Aryl and heteroaryl radicals may be substituted, for example, with $C_1$–$C_6$-alkyl, $C_1$–$C_3$-alkoxy, hydroxyl, carboxyl, sulfonyl, nitro, cyano or/and oxo. Furthermore, $R^1$ may have the meanings $COOR^3$, $CONR^3R^4$ or $COR^5$.

The $X^1$ group is a radical having electron donor or/and electron acceptor properties, preferably $NR^3R^4$, $OR^3$ $SR^3$, $COOR^3$, $CONR^3R^4$ or $COR^5$. $X^1$ is particularly preferably $NR^3R^4$. $R^3$ may be any organic radical or hydrogen. $R^4$ may be hydrogen or an unsubstituted or substituted alkyl, alkenyl or alkynyl radical, as described above.

$R^5$ may be hydrogen or an alkyl, alkenyl, alkynyl, carboxyalkyl, carboxyalkenyl, carboxyalkynyl, carboxy-aryl or carboxyheteroaryl radical. $R^5$ is preferably a space-filling radical and contains at least one aryl, heteroaryl, cycloalkyl or/and tert-alkyl group. Particular preference is given to phenyl radicals, substituted phenyl radicals, tert-alkyl radicals and cycloalkyl radicals, which may contain, where appropriate, substituents as defined above.

If $X^1$ has the meaning $NR^3R^4$ and $R^3$ and $R^4$ are in each case independently hydrogen or unsubstituted or substituted alkyl, alkenyl, alkynyl or heteroaryl radicals (see definition of $R^1$), $R^1$ has preferably a meaning different from hydrogen, particularly preferably $COOR^3$, $CONR^3R^4$ or $COR^5$, in particular $COOR^3$, $CONH_2$, $CO$—$COOR^5$ or CHO so that the compounds I are derivatives of guanidinophenylglycine.

$R^3$ is particularly preferably a group of the general formula (II):

in which
$X^2$ is NH, $NR^4$, O or S,
$X^3$ is NH, $NR^4$, O, S, CO, COO, CONH or $CONR^4$,
Y is $C(R^8)_2$,
$R^4$ is defined as in formula (I),
$R^7$ is H or an unsubstituted or substituted alkyl, alkenyl, alkynyl, aryl or/and heteroaryl radical or $—SO_2—R^9$,

$R^8$ is in each case independently H, halogen or an unsubstituted or substituted alkyl, alkenyl, alkynyl or aryl or/and heteroaryl radical,
$R^9$ is H or an unsubstituted or substituted alkyl, alkenyl, alkynyl, aryl or/and heteroaryl radical and
n is an integer from 0 to 2.
$X^2$ is preferably NH or O, particularly preferably O. $X^3$ is preferably NH or —O—. Y is preferably $CH_2$ or $CHR^8$, $R^8$ being preferably defined as $R^4$ in formula (I).
$R^7$ and $R^9$ are preferably defined as $R^5$ in formula (I).
$R^3$ is most preferably a group of the formula IIIa, IIIb or IIIc:

in which $R^7$ and $R^9$ are as defined in formula (II).

The substituents $R^7$ and $R^9$ contain, like $R^5$, preferably space-filling groups which may be selected from the group comprising unsubstituted or substituted aryl radicals, in particular phenyl and substituted phenyl radicals and unsubstituted or substituted branched alkyl, alkenyl or alkynyl radicals, in particular with tertiary carbon atoms such as tert-butyl or neopentyl, or unsubstituted or substituted cycloalkyl radicals, in particular bi- or tricycloalkyl radicals such as adamantyl.

Particularly high affinity and selectivity for uPA are also exhibited by compounds of the general formula (IV):

in which Ar, $X^1$, $R^2$ and m, on each occurrence,
independently may be identical or different and have a meaning as defined in the formulae (I), (II) and (IIIa–c).
The compounds of the formula (IV) contain two arylguanidino groups and are linked to one another via their substituents $CHR^1X^1$— which may be in each case identical or different.

Figure 1:
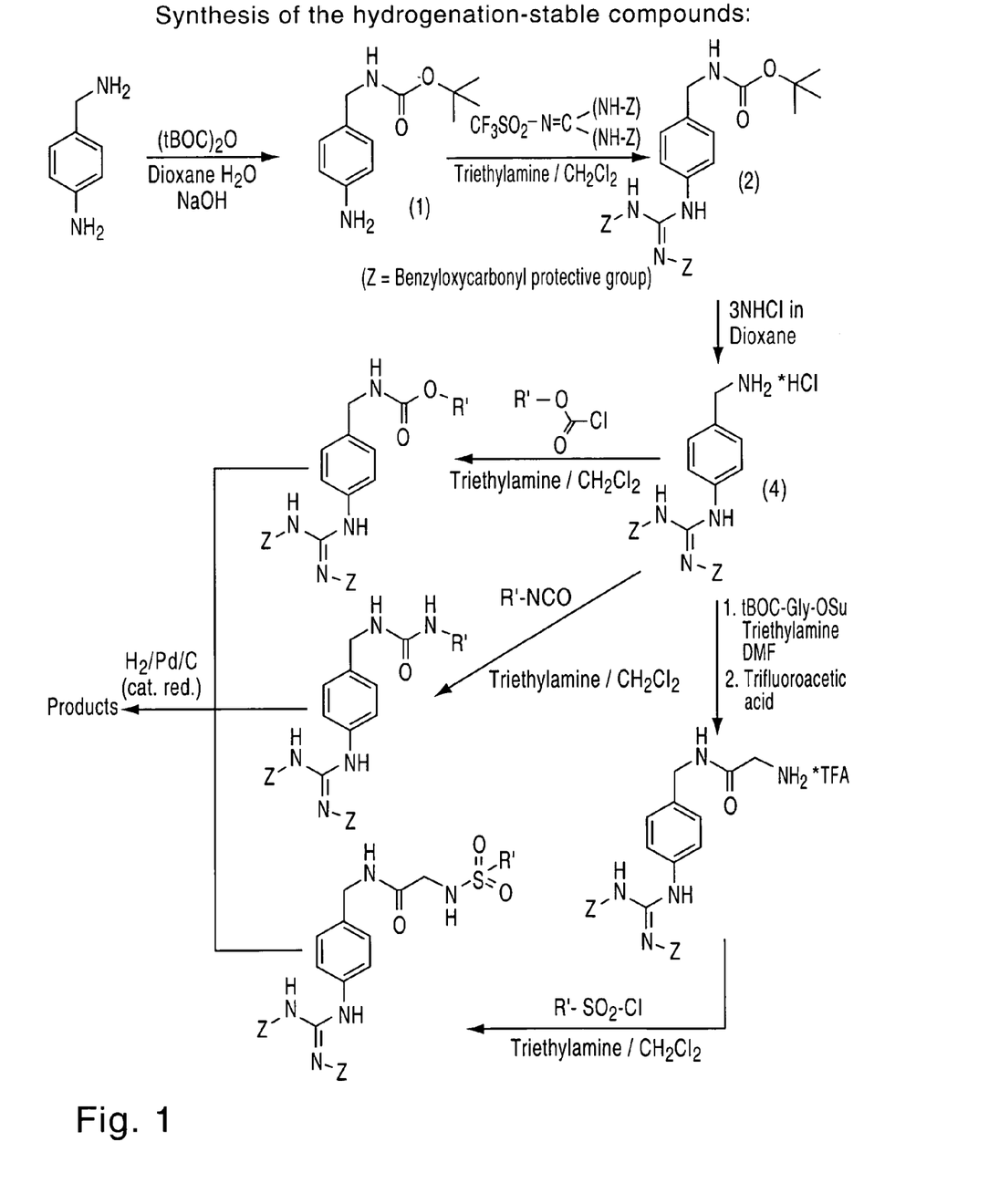
FIG. 1 shows a general reaction scheme for preparing hydrogenation-stable substances of the invention.
Figure 2:
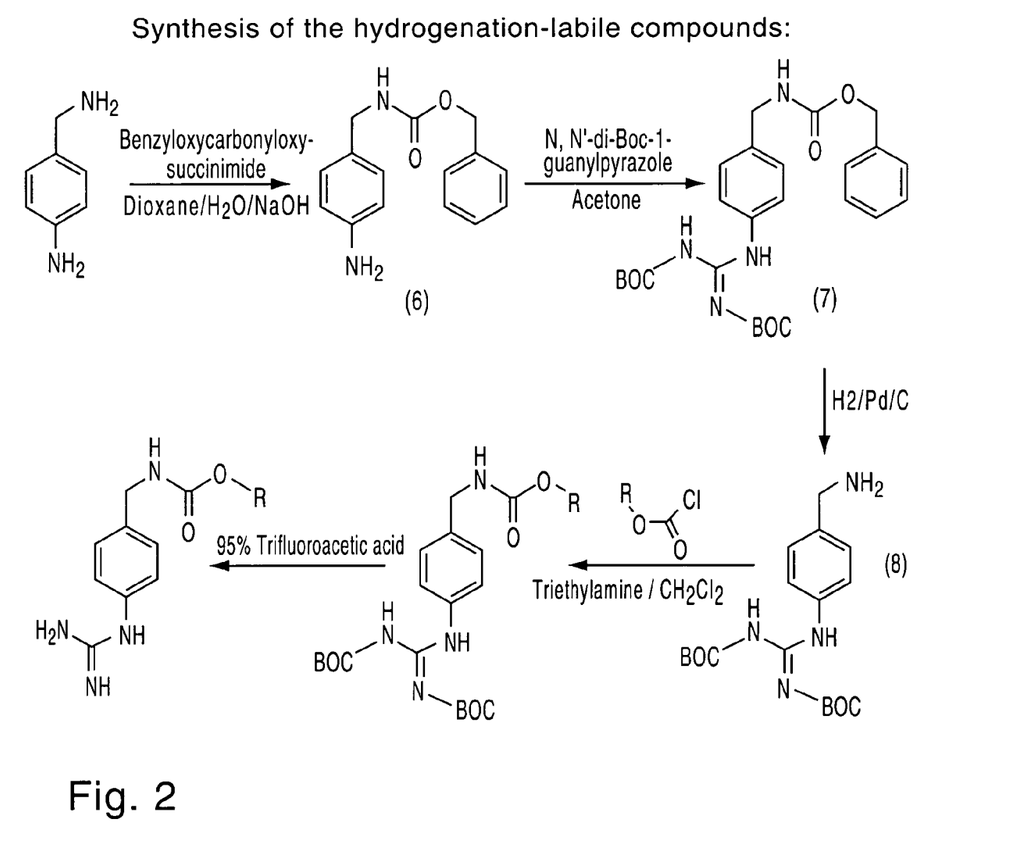
FIG. 2 shows a general reaction scheme for preparing hydrogenation-labile substances of the invention.

The compounds of the general formula (I) may be prepared, for example, starting from p-aminobenzylamine according to the reaction schemes shown in FIGS. 1 and 2. For example, 4-aminobenzylamine may be reacted with a protective reagent for amino groups, for example di-tert-butyl pyrocarbonate, to give a protected intermediate, 4-(N-Boc-aminomethyl)aniline (1), Boc meaning tert-butyloxy-carbonyl. The aromatic amino function of this compound can be reacted with a guanidinylation reagent, for example N,N'-di-Z-N''-triflylguanidine, resulting in 1-[4-(N-Boc-amino-methyl)phenyl-2,3-di-Z-guanidine (2), Z being benzyloxycarbonyl. This compound can be converted to 1-[4-(aminomethyl)phenyl]-2,3-di-Z-guanidinium hydrochloride (4) by removing the Boc protective group by cleavage. The compound (4) may in turn be reacted with reactive compounds such as, for example, chloroformic esters, isocyanates or N-hydroxysuccinimide esters to give the desired final products.

The preparation of hydrogenation-labile compounds is described in FIG. 2. 4-Aminobenzylamine can be reacted with a protective reagent for amino groups, for example benzyloxycarbonyloxysuccinimide to give a protected intermediate (6) and then with a further guanidinylation reagent, for example N,N'-di-Boc-1-guanylpyrazole, to give (7). This compound can be hydrogenated to give (8) and then be reacted with reactive compounds to give the desired final products.

Correspondingly, it is also possible to synthesize compounds in which $X^1$ has the meaning $OR^3$, $SR^3$, $COOR^3$, $CONR^3R^4$ or $COR^5$.

The urokinase inhibitors of the invention may be used, where appropriate, together with suitable pharmaceutical auxiliary agents or carriers for producing medicaments or in diagnostics. In this connection, administration in combination with other active substances, for example other urokinase inhibitors such as, for example, antibodies or/and peptides, is possible.

The medicaments may be administered in humans and animals topically, orally, rectally or parenterally, for example subcutaneously or intravenously, for example in the form of tablets, coated tablets, capsules, pellets, suppositories, solutions or transdermal systems such as plasters.

The compounds of the invention are suitable for controlling disorders which are associated with pathological overexpression of uPA or/and uPAR. They are, for example, capable of very effectively inhibiting the growth or/and spreading of malignant tumors and also metastasizing of tumors. It is possible to use the uPA inhibitors, where appropriate, together with other tumor agents or with other types of treatment, for example radiation or surgery. Furthermore, the inhibitors of the invention are also effective in other uPA-associated disorders.

uPA inhibitors of the invention are preferably characterized in that they have a $K_i$ which is at least two times, preferably at least five times and particularly preferably at least ten times and up to 1,000 times lower for uPA than for tPA. It is furthermore remarkable that the compounds of the invention only marginally affect blood clotting, since their $K_i$ values are too high for effective inhibition of thrombin, plasmin and factor Xa.

The inventive substances of the formula (I) may be used in the form of conjugates with physiologically effective substances, for example radiolabels or cytotoxic agents, e.g. chemotherapeutics such as cisplatin or 5-fluorouracil, or with peptides. Furthermore, it is also possible to incorporate the substances into the membrane of carrier vesicles, for example liposomes, and thus to make possible targeting of active substances enclosed in said carrier vesicles, for example cytotoxic agents such as doxorubicin.

The present invention provides a method for inhibiting urokinase in living creatures, in particular in humans, by administering an effective quantity of at least one compound of the formula (I). The dosage of the compound is commonly in the range from 0.01 to 100 mg/kg of body weight per day. The length of treatment depends on the seriousness of the disorder and may range from a single dose up to a treatment lasting several weeks or even several months, which may be repeated at intervals, where appropriate.

Finally, the present invention relates to novel arylguanidine derivatives of the general formula (I).

The invention is intended to be illustrated in more detail by the following examples and figures in which.

EXAMPLES

Materials and Methods

All solvents and reagents used for the synthesis of uPA inhibitors were of the highest commercially available quality and were, if necessary, further purified and dried by standard methods. Analytical HPLC was carried out on Nucleosil 100/C18 columns (Macherey-Nagel, Düren, Germany) using a linear acetonitrile/2% $H_3PO_4$ gradient (from 5:95 to 90:10 in 13 min). ESI-MS spectra were measured in a Perkin Elmer API 165 mass spectrometer.

Example 1

Synthesis of Acid-Labile Urethanes, for Example 4-(N-Boc-aminomethyl)phenylguanidine (3)

4-(N-Boc-Aminomethyl)aniline (1)

4-Aminobenzylamine (2 ml; 17.6 mmol) was dissolved in 1,4-dioxane (10 ml). An aqueous 2 N NaOH solution (17.6 ml; 35.2 mmol) was added with stirring. A solution of di-tert-butyl pyrocarbonate (3.08 g; 14.1 mmol) in 1,4-dioxane (30 ml) was added dropwise over 30 min and the reaction mixture was stirred at room temperature overnight. The solution was concentrated under reduced pressure to approximately 10 ml and extracted twice with ethyl acetate (30 ml). The combined organic phases were washed with aqueous 5% $KHSO_4$ (10 ml), aqueous 5% $NaHCO_3$, water and salt solution, dried over anhydrous $Na_2SO_4$ and evaporated under reduced pressure, the resulting product being a light yellow solid substance.

Yield: 2.38 g (76%); HPLC: $t_R$ 5.6 min; MS 223 $(M+H)^+$, calculated 222 (M).

1-[4-(N-Boc-Aminomethyl)phenyl]-2,3-di-Z-guanidine (2)

A solution of the compound (1) (500 mg; 2.24 mmol) and N,N'-di-Z-N"-triflylguanidine (1.04 g; 2.24 mmol) (Feichtinger et al., J. Org. Chem. 63 (1998), 3804–3805) in 5 ml of acetone was stirred vigorously at room temperature. After 10 min the product started to precipitate. After 2 h the product was filtered off, dried under reduced pressure and recrystallized from methanol, resulting in white crystals.

Yield: 1.065 g (89%); HPLC: $t_R$ 13.4 min; MS 533 $(M+H)^+$, calculated 532 (M).

4-(Boc-Aminomethyl)phenylguanidinium hydrochloride (3)

50 mg (0.107 mmol) of the compound (2) were dissolved in 5 ml of methanol, stirred and hydrogenated over a 10% palladium/activated carbon catalyst for 3 h. After removing the catalyst by filtration, the solvent was evaporated under reduced pressure. The residue was recrystallized from methanol/diisopropyl ether after adding one equivalent of HCl in 1,4-dioxane.

Yield: 28 mg (87%); HPLC: $t_R$ 7.1 min; MS 265 (M+H)$^+$, calculated 264 (M).

Example 2

Synthesis of Disubstituted Ureas Using 1-[4-(aminomethyl)phenyl]-2,3-di-Z-guanidinium hydrochloride (4) as Component, for Example 4-[3-(1-adamantyl)ureido]-phenylguanidinium hydrochloride (5)

1-[4-(Aminomethyl)phenyl]-2,3-di-Z-guanidinium hydrochloride (4)

1 g (1.878 mmol) of the compound (2) was dissolved at 0° C. in 20 ml of 3 N HCl (gas) in 1,4-dioxane and stirred at room temperature for 2 h. After evaporating the solvent, the crystalline product was obtained in virtually quantitative yield.

Yield: 872 mg (99%); HPLC: $t_R$ 10.2 min; MS 433 (M+H)$^+$, calculated 432 (M).

4-[3-(1-adamantyl)ureido]phenylguanidinium hydrochloride (5)

50 mg (0.107 mmol) of the compound (4), 17 mg (0.107 mmol) of adamantyl isocyanate and 45 µl (0.32 mmol) of triethylamine were dissolved in 1 ml of ethylene chloride. The reaction mixture was stirred at room temperature for 3 h. After evaporating the solvent under reduced pressure, the residue was dissolved in ethyl acetate (10 ml) and extracted three times with 0.1 N aqueous HCl. The organic phase was concentrated to dryness. The protective groups Z were removed as described for compound (3).

Yield: 15 mg (37%); HPLC: $t_R$ 8.6 min; MS 342 (M+H)$^+$, calculated 341 (M).

Example 3

Synthesis of Hydrogenation-Labile Compounds, for Example 4-[N-(4-nitrobenzyl-oxycarbonyl)aminomethyl]phenylguanidine (9)

4-(N-Z-Aminomethyl)aniline (6)

4-Aminobenzylamine (1 ml; 8.82 mmol) was dissolved in 10 ml of 1,4-dioxane. An aqueous 2 N solution of NaOH (8.8 ml; 17.64 mmol) was added with stirring. Then a solution of benzyloxycarbonyloxysuccinimide (1.978 g; 7.938 mmol) in 10 ml of 1,4-dioxane was added dropwise over 15 min, and the reaction mixture was stirred at room temperature for 5 h. The solution was concentrated under reduced pressure to approximately 10 ml and extracted twice with 30 ml of ethyl acetate. The combined organic phases were washed with aqueous 5% strength NaHCO$_3$ solution, water and salt solution, dried over anhydrous Na$_2$SO$_4$, concentrated and dried under reduced pressure, the resulting product being a light yellow solid substance.

Yield: 1.8 g (88%); HPLC: $t_R$ 6.8 min; MS 257 (M+H)$^+$, calculated. 256 (M).

1-[4-(N-Z-Aminomethyl)phenyl]-2,3-di-Boc-guanidine (7)

A solution of 495 mg (1.93 mmol) of the compound (6) and 599 mg (1.93 mmol) of N,N'-di-Boc-1-guanylpyrazole (Bernatowicz et al., Tetrahedron Lett. 34 (1993), 3389–3392) in 5 ml of acetone was stirred at room temperature for 3 days. After evaporating the solvent, the residue was dissolved in. 50 ml of diethyl ether, washed with aqueous 5% KHSO$_4$ solution, water and salt solution and dried over anhydrous Na$_2$SO$_4$. Evaporating the diethyl ether under reduced pressure resulted in a light yellow foam.

Yield: 670 mg (70%); HPLC: $t_R$ 12.1 min; MS 499 (M+H)$^+$, calculated 498 (M).

1-(4-Aminomethyl)phenyl-2,3-di-Boc-guanidine hydrochloride (8)

The compound (8) was obtained by catalytic hydrogenation of 600 mg (1.2 mmol) of the compound (7) in ethanol over a 10% palladium/activated carbon catalyst for 1 h. After filtration of the catalyst, the solvent was evaporated under reduced pressure, resulting in an oil which was recrystallized from isopropanol/diisopropyl ether after adding 1 equivalent of HCl in 1,4-dioxane.

Yield: 450 mg (91%); HPLC: $t_R$ 8.1 min; MS 365 (M+H)$^+$, calculated 364 (M).

4-[N-(4-Nitrobenzyloxycarbonyl)aminomethyl]phenyl-guanidine hydrochloride (9)

A solution of 50 mg (0.125 mmol) of the compound (8), 27 mg (0.125 mmol) of 4-nitrobenzyl chloroformate and 52 µl (0.375 mmol) of triethylamine in 1 ml, of methylene chloride was stirred at room temperature for 3 h. After evaporating the solvent, the residue was dissolved in 30 ml of ethyl acetate and washed three times with 0.5 N aqueous HCl. After evaporating the ethyl acetate, the residue was dissolved in 95% trifluoroacetic acid and stirred for 1 h. After evaporating the solvent, the product was recrystallized from ethanol/diisopropyl ether.

Yield: 35 mg (60%); HPLC: $t_R$ 8.1 min; MS 344 (M+H)$^+$, calculated 343 (M).

Example 4

In-Vitro Inhibition of Urokinase by Selected Compounds of the Formula I

The uPA inhibitor activity was determined by incubating 200 µl of Tris buffer (0.05 mol/l, containing the inhibitor, 0.154 mol/l NaCl, 5% ethanol, pH 8.0), 25 µl of substrate (Pefachrome UK or BZ-β-Ala-Gly-Arg-pNA in H$_2$O; Pentapharm Ltd, Basle, Switzerland) and 50 µl of sc-urokinase (Ribosepharm GmbH, Haan, Germany) or another corresponding protease at 25° C. After 3 min, the reaction was interrupted by adding 25 µl of acetic acid (50%) and absorbance at 405 nm was determined by means of a microplate reader (MR 5000, Dynatech, Denkendorf, Germany). The K$_i$ values were determined by linear regression according to Dixon by means of a computer program. The K$_i$ values are the average of at least three determinations, and the standard deviation was below 25%. The inhibitors assayed and their inhibition constants for various proteases are listed in table 1 below:

TABLE 1

| Inhibitor | Name | Ki [μM] | | | | |
|---|---|---|---|---|---|---|
| | | uPA | Plasmin | Thrombin | Trypsin | F Xa |
| (ethyl carbamate benzyl guanidine structure) | ST 269 | 27 | >1000 | >1000 | >1000 | >1000 |
| (aminomethyl phenyl guanidine structure) | ST 270 | 46 | >1000 | >1000 | >1000 | >1000 |
| (tert-butyl carbamate benzyl guanidine structure) | ST 242 | 36 | >1000 | >1000 | >1000 | >1000 |
| (adamantyl carbamate benzyl guanidine structure) | ST 274 | 23 | >1000 | >1000 | >1000 | >1000 |
| (adamantyl urea benzyl guanidine structure) | ST 293 | 2,4 | >1000 | 600 | 46 | >1000 |
| (acetamido thiazole sulfonamide benzyl guanidine structure) | ST 282 | 240 | >1000 | >1000 | >1000 | >1000 |
| (aminophenyl guanidine structure) | ST 267 | >1000 | >1000 | >1000 | >1000 | >1000 |

TABLE 1-continued

| Inhibitor | Name | Ki [μM] | | | | |
| --- | --- | --- | --- | --- | --- | --- |
| | | uPA | Plasmin | Thrombin | Trypsin | F Xa |
| (structure) | ST 296 | 22 | >1000 | >1000 | 42 | >1000 |
| (structure) | ST 294 | 37 | >1000 | >1000 | >1000 | >1000 |
| (structure) | ST 298 | 42 | >1000 | >1000 | 37 | >1000 |
| (structure) | ST 270 | 46 | >1000 | >1000 | >1000 | >1000 |
| (structure) | ST 271 | 51 | >1000 | >1000 | >1000 | >1000 |
| (structure) | ST 275 | >1000 | >1000 | >1000 | >1000 | >1000 |
| (structure) | ST 273 | 52 | 130 | >1000 | >1000 | >1000 |

TABLE 1-continued

| Inhibitor | Name | Ki [μM] | | | | |
| --- | --- | --- | --- | --- | --- | --- |
| | | uPA | Plasmin | Thrombin | Trypsin | F Xa |
| (structure) | ST 301 | 29 | 170 | >1000 | >1000 | 330 |
| (structure) | ST 311 | 12 | ??? | >1000 | 200 | >1000 |
| (structure) | ST 312 | 2,8 | ??? | >1000 | 100 | >1000 |
| (structure) | ST 313 | 35 | ??? | >1000 | ??? | >1000 |
| (structure) | ST 315 | 11 | ??? | >1000 | 200 | >1000 |

The compounds ST293, 312 and 315 have a $K_i$ value for uPA of >1,000 μm.

The compounds denoted as ST293 and ST312 proved to be particularly effective and selective inhibitors.

The invention claimed is:

1. A method for the treatment of breast cancer, comprising administering to a patient in need of such treatment an effective amount of a pharmaceutical composition comprising at least one compound of the formula (I)

(I)

in which

Ar is an aromatic or heteroaromatic ring system having a single ring;

$X^1$ is $NR^3R^4$, $OR^3$, $SR^3$, $COOR^3$, $CONR^3R^4$ or $COR^5$, where $R^3$ is H or a group of the formula II, IIIa, IIIb or IIIc:

(II)

(IIIa)

(IIIb)

-continued (IIIc)

where
X² is NH, NR⁴, O or S,
X³ is NH, NR⁴, O, S, CO, COO, CONH or CONR⁴,
Y is C(R⁸)₂,
R⁴ is H or an alkyl, alkenyl or alkynyl radical,
R⁷ is H or an alkyl, alkenyl, alkynyl, aryl or/and heteroaryl radical or —SO₂—R⁹,
R⁸ in each case independently H, halogen or an alkyl, alkenyl, alkynyl, aryl or/and heteroaryl radical,
R⁹ is H or an alkyl, alkenyl, alkynyl, aryl or/and heteroaryl radical and
n is an integer from 0 to 2,
R⁵ is H, an alkyl, alkenyl, alkynyl, carboxyalkyl, carboxyalkenyl, carboxyalkynyl, carboxyaryl or carboxyheteroaryl radical;
R² is halogen, C(R⁶)₃, C₂(R⁶)₅, OC(R⁶)₃ or OC²(R⁶)₅, where
R⁶ is in each case independently H or halogen and
m is an integer from 0 to 4;
or salts of said at least one compound.

2. The method according to claim 1, wherein the treatment comprises controlling pathological overexpression of urokinase and/or urokinase receptor in a patient.

3. The method according to claim 1, wherein the treatment comprises controlling the formation of metastases in a patient.

4. A pharmaceutical kit for the treatment of breast cancer comprising the following components:
(a) at least one first anti-tumor agent of the formula (I)

(I)

in which
the substituents —CH₂X¹ and —NHC(NH)NH₂ are arranged in a para position to each other;
Ar is an aromatic or heteroaromatic ring system having a single ring;
X¹ is NR³R⁴, OR³, SR³, COOR³ CONR³R⁴ or COR⁵, where
R³ is H or a group of the formula II, IIIa, IIIb or IIIc:

(II)

-continued (IIIa)

(IIIb)

(IIIc)

where
X² is NH, NR⁴, O or S,
X³ is NH, NR⁴, O, S, CO, COO, CONH or CONR⁴,
Y is C(R⁸)₂,
R⁴ is H or an alkyl, alkenyl or alkynyl radical,
R⁷ is H or an alkyl, alkenyl, alkynyl, aryl or/and heteroaryl radical or —SO₂—R⁹,
R⁸ is in each case independently H, halogen or an alkyl, alkenyl, alkynyl, aryl or/and heteroaryl radical,
R⁹ is H or an alkyl, alkenyl, alkynyl, aryl or/and heteroaryl radical and
n is an integer from 0 to 2,
R⁵ is H, an alkyl, alkenyl, alkynyl, carboxyalkyl, carboxyalkenyl, carboxyalkynyl, carboxyaryl or carboxyheteroaryl radical;
R² is halogen, C(R⁶)₃, C₂(R⁶)₅, OC(R⁶)₃ or OC²(R⁶)₅, where
R⁶ is in each case independently H or halogen; and
m is an integer from 0 to 4;
or salts of said at least one compound, and a second anti-tumor agent, wherein said first anti-tumor agent and said second anti-tumor agent are in separate containers.

5. A kit according to claim 4, wherein the halogen of R⁶ in said compound of formula I is F.

6. A kit according to claim 4, wherein said second anti-tumor agent is cisplatin, 5-fluorouracil or a peptide.

7. A method for the treatment of breast cancer comprising administering to a patient in need of such treatment an effective amount of a compound of the formula (I)

(I)

in which
the substituents —CH₂X¹ and —NHC(NH)NH₂ are arranged in a para position to each other;
Ar is an aromatic or heteroaromatic ring system having a single ring;

$X^1$ is $NR^3R^4$, $OR^3$, $SR^3$, $COOR^3$, $CONR^3R^4$ or $COR^5$,
where
$R^3$ is H or a group of the formula II, IIIa, IIIb or IIIc:

where
$X^2$ is NH, $NR^4$, O or S,
$X^3$ is NH, $NR^4$, O, S, CO, COO, CONH or $CONR^4$,
Y is $C(R^8)_2$,
$R^4$ is H or an alkyl, alkenyl or alkynyl radical,
$R^7$ is H or an alkyl, alkenyl, alkynyl, aryl or/and heteroaryl radical or $-SO_2-R^9$,
$R^8$ is in each case independently H, halogen or an alkyl, alkenyl, alkynyl, aryl or/and heteroaryl radical,
$R^9$ is H or an alkyl, alkenyl, alkynyl, aryl or/and heteroaryl radical and
n is an integer from 0 to 2,
$R^5$ is H, an alkyl, alkenyl, alkynyl, carboxyalkyl, carboxyalkenyl, carboxyalkynyl, carboxyaryl or carboxyheteroaryl radical;
$R^2$ is halogen, $C(R^6)_3$, $C_2(R^6)_5$, $OC(R^6)_3$ or $OC^2(R^6)_5$, where
$R^6$ is in each case independently H or halogen; and
m is an integer from 0 to 4, with the provisos that
when Ar=phenyl, m=O, then $CH_2X^1$ is not $CH_2COOH$,
when Ar=phenyl, m=0, $X^1=NR^3R^4$ with $R^4$=H and $R^3$=—$COOR^7$ with $R^7$=tertbutyl
and m=0, then the compound of formula (I) is not in the hydrochloride salt form,
and
when Ar=phenyl, m0 and $X^1=NH_2$, then the compound of formula (I) is not in
the bistrifluoroacetate salt form.

8. The method of claim 7, wherein Ar is a benzene ring.
9. The method of claim 8, in which the substituents —$CH^?X^1$ and —$NHC(NH)NH_2$ are arranged in a para position to each other.
10. The method of claim 7, in which $R^7$ and $R^9$ are at least one aryl, at least one tertiary alkyl radical or at least one cycloalkyl radical.
11. The method of claim 10, in which $R^7$ and $R^9$ are phenyl radicals.
12. The method of claim 10, in which $R^7$ and $R^9$ are bicyloalkyl radicals.
13. The method of claim 10, in which $R^7$ and $R^9$ are adamantyl.
14. A method according to claim 7, wherein 0.01 to 100 mg of said compound is administered per kg of body weight per day.
15. A method according to claim 14, wherein 0.1 to 100 mg of said compound is administered per kg of body weight per day.
16. The method according to claim 7, wherein the halogen of $R^6$ in said compound of formula I is F.
17. The method according to claim 1, wherein the substituents —$CH_2X^1$ and —$NHC(NH)NH_2$ are arranged in a para position to each other, and with the provisos that
when Ar=phenyl, m=O, then $CH_2X^1$ is not $CH_2COOH$,
when Ar=phenyl, m=0, $X^1=NR^3R^4$ with $R^4$=H and $R^3$=—$COOR^7$ with $R^7$=tertbutyl and
m=0, then the compound of formula (I) is not in the hydrochloride salt form, and
when Ar=phenyl, m0 and $X^1=NH_2$, then the compound of formula (I) is not in the bistrifluoroacetate salt form.
18. The method of claim 17, in which Ar is a benzene ring.
19. The method of claim 18, in which the substituents —$CH^?X^1$ and —$NHC(NH)NH_2$ are arranged in a para position to each other.
20. The method of claim 17, in which $R^7$ and $R^9$ are at least one aryl radical, at least one tertiary alkyl radical or at least one cycloalkyl radical.
21. The method of claim 20, in which $R^7$ and $R^9$ are phenyl radicals.
22. The method of claim 20, in which $R^7$ and $R^9$ are bicyloalkyl radicals.
23. The method of claim 20, in which $R^7$ and $R^9$ are adamantyl.
24. The method according to claim 17, wherein the halogen of $R^6$ in said compound of formula I is F.
25. The method according to claim 17, wherein the treatment comprises controlling the formation of metastasis in a patient.
26. The method of claim 25, wherein Ar is a benzene ring.
27. The method of claim 26, in which the substituents —$CH^?X^1$ and —$NHC(NH)NH_2$ are arranged in a para position to each other.
28. The method of claim 25, in which $R^7$ and $R^9$ are at least one aryl, at least one tertiary alkyl radical or at least one cycloalkyl radical.
29. The method of claim 28, in which $R^7$ and $R^9$ are phenyl radicals.
30. The method of claim 28, in which $R^7$ and $R^9$ are bicyloalkyl radicals.
31. The method of claim 30, in which $R^7$ and $R^9$ are adamantyl.
32. A method for the treatment of breast cancer comprising administering to a patient in need of such treatment an effective amount of at least one compound of the formula (IV)

in which
$X^1$ is in each case independently $NR^3R^4$, $OR^3$, $SR^3$, $COOR^3$, $CONR^3R^4$ or $COR^5$,
where
$R^3$ is in each case independently H or any organic radical,
$R^4$ is in each case independently H or an alkyl, alkenyl or alkynyl radical;

Ar is in each case independently an aromatic or heteroaromatic ring system, $R^5$ is H, an alkyl, alkenyl, alkynyl, carboxyalkyl, carboxyalkenyl, carboxyalkynyl, carboxyaryl or carboxyheteroaryl radical;

$R^2$ is in each case independently halogen, $C(R^6)_3{}^3$, $C_2(R^6)_5$, $OC(R^6)_3$ or $OC_2(R^6)_5$, where $R^6$ is in each case independently H or halogen; and m is an integer from 0 to 4;

or salts of said compound.

33. A method for the treatment of breast cancer, comprising administering to a patient in need of such treatment an effective amount of a pharmaceutical composition comprising at least one compound of the formula (IV)

in which $X^1$ is in each case independently $NR^3R^4$, $OR^3$, $SR^3$, $COOR^3$, $CONR^3R^4$ or $COR^5$, where $R^3$ is in each case independently H or any organic radical, $R^4$ is in each case independently H or an alkyl, alkenyl or alkynyl radical;

Ar is in each case independently an aromatic or heteroaromatic ring system, $R^5$ is H, an alkyl, alkenyl, alkynyl, carbokyalkyl, carboxyalkenyl, carboxyalkynyl, carboxyaryl or carboxyheteroaryl radical;

$R^2$ is in each case independently halogen, $C(R^6)_3{}^3$, $C_2(R^6)_5$, $OC(R^6)_3$ or $OC_2(R^6)_5$, where $R^6$ is in each case independently H or halogen; and m is an integer from 0 to 4;

or salts of said at least one compound.

34. The method according to claim 33, wherein the treatment comprises controlling pathological overexpression of urokinase or/and urokinase receptor in a patient.

35. The method according to claim 33, wherein the treatment comprises controlling the formation of metastases in a patient.

36. The method of claim 7 comprising administering to said patient the compound of formula or a salt thereof.

37. The method of claim 7 comprising administering to said patient the compound of
formula or a salt thereof.

38. The method of claim 29 comprising administering to said patient the compound of formula or a salt thereof.

* * * * *